United States Patent [19]
Garris

[11] Patent Number: 5,971,945
[45] Date of Patent: Oct. 26, 1999

[54] ULNAR SUPPORT SPLINT

[76] Inventor: Cynthia G. Garris, 1522 Dairy Rd., Charlottesville, Va. 22903

[21] Appl. No.: 08/994,403

[22] Filed: Dec. 19, 1997

[51] Int. Cl.$^6$ ........................................................ A61F 5/00
[52] U.S. Cl. .................................................. 602/21; 602/6
[58] Field of Search .............................. 602/5–8, 20–22

[56] References Cited

U.S. PATENT DOCUMENTS

| | | | |
|---|---|---|---|
| 1,917,794 | 7/1933 | Brown | 602/22 |
| 2,477,126 | 7/1949 | Hartmann | 602/22 X |
| 3,680,549 | 8/1972 | Lehneis et al. | 602/23 X |
| 4,382,439 | 5/1983 | Shen | 602/21 |
| 4,732,142 | 3/1988 | Hurlburt et al. | 602/21 |
| 5,279,545 | 1/1994 | Reese, Sr. | 602/21 |
| 5,415,623 | 5/1995 | Cherubini | 602/7 |
| 5,520,626 | 5/1996 | Schaeffer | 602/22 |
| 5,746,707 | 5/1998 | Eck | 602/21 |

*Primary Examiner*—Richard J. Apley
*Assistant Examiner*—Denise Pothier
*Attorney, Agent, or Firm*—Sheldon H. Parker

[57] ABSTRACT

The ulnar support splint is formed of a continuous spiral having a first end, a midpoint and a second end. The splint can be made of a semi-rigid material being molded to the user's hand. The splint provides lateral support to a user's fingers through at least three points of contact, including the ulnar medial side of at least one finger, the web space between the user's thumb and metacarpophalangeal joint of the user's index finger and the user's wrist distal the user's ulnar styloid. A method for providing lateral support to the fingers using the splint applies pressure at the least three points creating counterbalancing pressure points.

22 Claims, 2 Drawing Sheets

ULNAR SUPPORT SPLINT

BACKGROUND OF THE INVENTION

1. Field of the Invention

This invention relates to orthopaedic splint type devices for the hand used to align the proximal phalanges when necessary because of ulnar drift.

2. Description of the Prior Art

Rheumatoid arthritis is an incurable disease which affects a large number of individuals to varying degrees. In severe cases, the disease is both painful and crippling. Due to the incapacitive nature of the disease, various adaptive equipment and splints exist in the prior art to assist individuals in dealing with the effects of this disease.

When the hands become involved in the arthritic disease process, internal forces in the hand and fingers change due to pain, inflammation and swelling. This creates dynamic and static imbalances which result in deformities. Specifically, as the tendons and ligaments around the joint become over stretched and the bone structure of the joint deteriorates due to the disease, the joints become very unstable in all directions through the full range of flexion and extension. Chronic pain and general muscle weakness exacerbate the problem of joint instability to the point of serious loss of function in the rheumatoid hand.

When joint instability occurs in the lateral plane, it frequently results in ulnar deviation of the fingers at the metacarpophalangeal joints (ulnar drift). Specifically, ulnar drift results from the degradation due to disease or injury of the structures holding the flexor and/or extensor tendons in normal placement. Following this degradation, the tendons slip from their normal position toward the ulnar side of the hand. During normal grasp and release hand movement, the displaced tendons exert a lateral torque in the ulnar direction about the metacarpophalangeal joints, which results in ulnar medial deviation or ulnar drift of the phalanges. Ulnar drift causes decreased prehension, loss of grip strength and unacceptable cosmesis.

Furthermore, when ulnar drift occurs, the head of the second metacarpal bone of the index finger usually protrudes due to atrophy of the interosseous muscle. This bony protrusion must be avoided on the radial side of the hand when splinting, because it is painful when splints and/or straps rest on the protrusion and skin breakdown frequently occurs.

Prior art splints have attempted to address the problem of ulnar drift. They are typically palmar or dorsal hand based splints with padding and finger separators, such as disclosed in Barber, "Ulnar Deviation Splint," U.S. Pat. No. 4,558,694. The '694 patent, from the user's standpoint, has many drawbacks to the disclosed device. The use of hook and loop material requires more physical grip strength than many arthritis patients have in their fingers. Further the finger separators maintain the user's fingers in an abducted (separated) position which is awkward for performing normal everyday activities. Furthermore, the straps of the device simply hold the hand in relation to itself. There are no other areas of the hand or arm which are used to stabilize the hand and prevent ulnar drift. Prior to the Barber patent, Czap, "Ulnar Drift Splint," U.S. Pat. No. 3,299,887, in fact suggests a hinged mechanism to support laterally deviating fingers. Unfortunately, these prior art splints fail to provide sufficient leverage to correct ulnar drift.

As discussed above, when ulnar drift occurs, the fingers deviate in a lateral plane, with the axis of deviation being at the metacarpophalangeal joints. To correct this deformity, the splint needs to contact the affected area in three distinct and sufficiently separate areas to allow corrective leverage.

Palmar and dorsal hand based splints of the prior art are short, rotating when ulnarly deviating fingers push against the distal end of the splint. As the splint rotates, the distal edge on the radial side of the splint digs into the neck of the metacarpal bone just proximal to the head. This area is frequently recessed due to atrophy of the interosseous muscle, and it is very painful to have a splint either digging in proximal to the head of the metacarpal bone or resting directly on the lateral side of the metacarpal joint. Furthermore, splints resting on, and/or digging into, this area causes pressure sores and skin breakdown. Additionally, prior art splints tend to be bulky, abduct (spread apart) the fingers and have straps which make donning and doffing the splint difficult for individuals with limited hand function and grip strength. The ulnar support splint of the present invention overcomes the deficiencies of the prior art by providing a splint of sufficient overall length to provide corrective forces in the lateral plane.

SUMMARY OF THE INVENTION

A spiral splint is disclosed for providing lateral support for a user's fingers, such as in cases where the tendons of the hand slip from the metacarpophalangeal joints resulting in ulnar medial deviation. The spiral of the splint contacts the ulnar and radial areas of the hand and comprises at least one finger support member, each of which can conform to the contour of the finger and in contact with the finger's medial side. The finger supports can encircle the finger, with one or more of the supports being padded at the point of contact. A palmar support, curved to conform to the user's hand, engages the user's palm directly under the metacarpophalangeal joints. A radial arc conforms to, and engages, the radial area of the user's hand distal to the thumb and proximal the metacarpophalangeal joint of the index finger. A curved dorsum support angles across the hand's dorsum to a proximal arc which engages the ulnar side of the hand distal the ulnar styloid. A wrist support engages the user's forearm proximal the wrist and thumb carpometacarpal joint. The splint should avoid any contact with the radial side of the metacarpophalangeal joint of the index finger.

In one embodiment the splint is one contiguous piece of semi-rigid material, such as plastic or metal covered with a resilient material. Alternatively, the splint can be manufactured from two or more pieces which are affixed to one another at their ends. A hinged member can be attached to the wrist support and to engage the forearm. Additional securing straps can be provided extending from one of the finger supports member to the dorsum support.

Lateral support is provided for the fingers by contacting at least three points of the hand. These three points include one or more of said finger's ulnar medial sides; the web space between the thumb and the metacarpophalangeal joint of the index finger, and the wrist distal to the ulnar styloid. This placement allows the lateral force created by the fingers to be countered by contact of the splint at the web space. The lateral force created by the web space is then countered by contact of the splint at the ulnar styloid. These points of contact distribute the force required to support the fingers along the hand and wrist.

DESCRIPTION OF THE PREFERRED EMBODIMENT

The disclosed invention overcomes the problems associated with the foregoing prior art patents and miscellaneous devices by providing a device which allows the hand and wrist to provide additional support and leverage to the deviating fingers. The three areas of leverage are the ulnar medial side of one or more fingers, the web space between the thumb and the radial side of the metacarpophalangeal joint of the index finger and the wrist distal to the ulnar styloid. By contacting the affected area at these three distinct and sufficiently separate areas, a lateral corrective force can by applied which holds the fingers in proper alignment. The splint is light in weight, low in cross-sectional profile, does not have straps and can be donned and doffed without tools by spiraling around the arm. It is unobtrusive, easy to wear and allows the wearer to use finger and wrist splints in conjunction the ulnar support splint when necessary. Possibly most importantly, the disclosed splint can be worn while performing everyday tasks, such as driving, typing, writing, etc.

As discussed above, when ulnar drift occurs, the fingers deviate in a lateral plane, with the axis of deviation being at the metacarpophalangeal joints. To effectively correct this deformity, the splint needs to contact the affected area in three distinct and sufficiently separate areas to allow corrective leverage.

Figure 1:
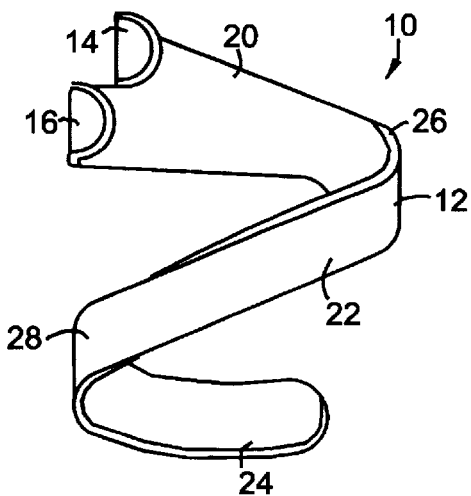
FIG. 1 illustrates the curved splint ready to be placed on the user's hand.
Figure 2:
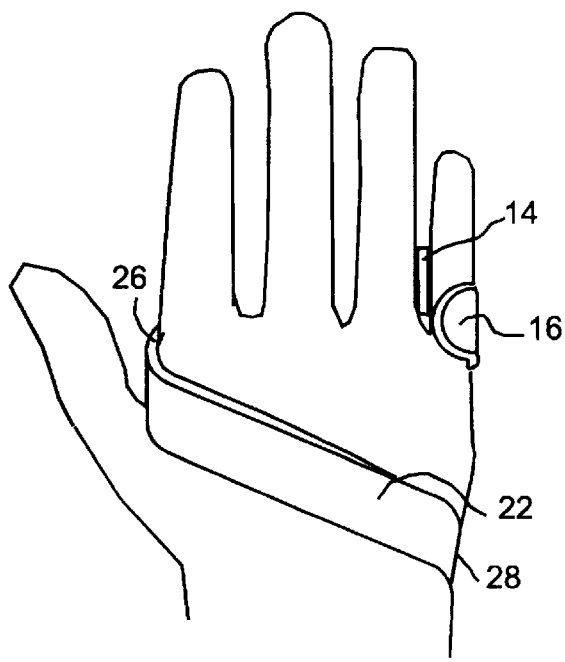
FIG. 2 is a view of the back of the user's hand wearing the splint of FIG. 1.
Figure 3:
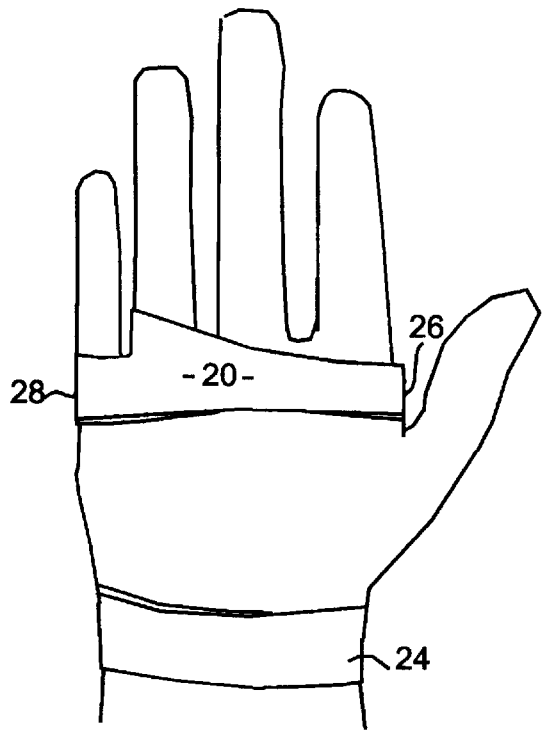
FIG. 3 is a view of the palmar area of the user's hand wearing the splint of FIG. 1.

As illustrated in FIGS. 1–3, the ulnar support splint 10 is comprised of a contiguous band or strip of thermoplastic or metal material which has been spiraled to wrap around the hand and wrist. Although in the illustrated embodiment, the splint 10 is a single piece of material, for ease of description the splint 10 has been divided in sections, finger supports 14 and 16; palmar support 20; dorsum support 22; and wrist support 24. At one end of the body 12, finger supports 14 and 16 are formed which contact the ulnar medial side of the little finger, and one or more additional fingers. In the illustrated embodiment, only the little finger and the adjacent ring finger are provided with supports. It should be noted, however, that separate lateral support may be provided for any one finger or for all fingers of the splinted hand, however in the preferred embodiment, lateral supports are provided for the ring and little fingers only. Research has shown that the index and middle fingers are sufficiently supported in the lateral plane by laying against the supported ring and little fingers and the resulting splint is less bulky and restrictive of normal hand movement. It has also been found that to provide maximum support, the little finger support 16 must be included. From the finger supports 14 and 16, the body 12 continues to a palmar support 20, proceeds around the hand to the dorsum support 22 and ends at the wrist support 24.

The finger supports 14 and 16 are formed to provide lateral support to the affected finger(s) by being positioned and held comfortably and firmly, but not forcefully, against the ulnar medial side of the proximal phalanx(s). The finger support 16 should have sufficient width to provide support and comfort. If any of the finger supports are too narrow, they will tend to dig into the user's hand, therefore being quite uncomfortable, and will provide little support to prevent ulnar drift. To provide optimum support, the placement of the little finger support 16 must be such that the distal edge of the support 16 must extend past the MCP joint of the small finger. The remaining finger supports 14 must fall distal to the web space between the fingers. Preferably, the supports do not extend to, or beyond, the proximal interphalangeal (PIP) joint of the supported finger(s) so that flexion of the PIP joints is not impeded.

The finger supports 16 should be thin enough to fit comfortably between the fingers without abducting the fingers, while sufficiently thick to provide slightly yielding, but basically firm, support of the fingers while the hand and fingers are being used for normal activities of daily living. Each of the finger support(s) 14 and 16 should extend from the attachment point on the palmar support 20 between the fingers and toward the back of the hand a sufficient distance to provide lateral support for each finger. In the preferred embodiment, each of the finger supports 14 and 16 extend far enough to comfortably cradle the fingers. The supports 14 and 16 are preferably semi-circular to match the round curvature of the finger, extending partially around each finger.

The palmar support 20 is slightly bowed to match the palmar arch and rests comfortably and firmly against the palm of the hand directly under the MCP joints. The MCP joints of hands where ulnar deviation is occurring are typically subluxed (dislocated). When the subluxed MCP joints are supported by the palmar support 20 of the splint, they tend to be pushed back into alignment from their subluxed position which decreases the pain associated with subluxation and allows the hand to look and function more normally.

The radial arc 26 contacting the hand between the thumb and the radial side of the MCP joint of the index finger is extremely important in both function and placement and serves as the fulcrum point of the splint 10. The finger supports 14 and 16 support and align the fingers by providing a radial force which counters the fingers tendency to ulnarly deviate. This force is transmitted by the design of the splint 10 to the fulcrum point at the arced band 26, where the radial force counters the ulnar force applied by the fingers. The force, or pressure, is further transmitted to the proximal arc 28 of the splint 10 where a radial force subsequently countered by the contact of the splint with the wrist distal the ulnar styloid.

Angling and placement of the radial arc 26 is critical as the splint 10 should contact the hand in the web space between the thumb and the metacarpophalangeal joint (MCP) of the index finger, then dorsum support 22 diagonally crosses the dorsum of the hand to the proximal arc 28. The proximal arc 28 preferably lies on the medial side of the wrist distal to the ulnar styloid; to allow for comfort and maximum freedom of movement. The splint 10 finally is formed around and in contact with the wrist support 24 lying on the arm proximal to the wrist. Care should be taken to avoid contact between the radial arc 26 and the radial side of the MCP joint and head of the metacarpal bone. This achieved by angling the dorsum support 22 and radial arc 26 diagonally away from the joint.

The dorsum support 22 falls diagonally across the back of the hand, comfortably following the curvature of the hand until it passes around the wrist on the ulnar side, distal the ulnar styloid. Finally, the wrist support 24 lies on the volar surface of the forearm, partially encircling of the arm and ending just proximal to the carpometacarpal (CMC) joint of the thumb.

When fitted for use by an ordinary patient, the splint will spiral around the hand, fit flush against the skin and provide comfortable and unobtrusive support for the fingers by holding the supported fingers in a normal and cosmetically acceptable position. The supported fingers are maintained in alignment while at rest and during normal activities. Such support improves prehension and grip strength while reducing pain and fatigue.

Figure 4:
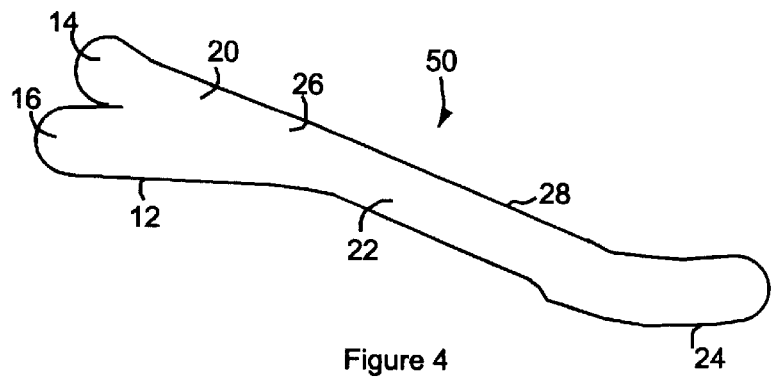
FIG. 4 is a plan view of the pattern used to make the splint of FIG. 1.

FIG. 4 illustrates the ulnar support splint pattern prior to being custom fitted for the patient. The curved pattern 50 is a design which can be utilized with various thermoplastic or metal materials to delineate a one dimensional shape which can be formed into the ulnar support splint of the general design and function disclosed here. A flat sheet of material, when cut out in the pattern disclosed here, may be formed through the use of heat and/or pressure into the shape of the ulnar support splint.

The component parts of the splint pattern 50 are similar to those described in the preferred embodiment, although they are necessarily flat in the pattern. The little finger support 16, finger support 14, the palmar support 20, the radial arc 26 which proceeds around the radial side of the hand between the thumb and the metacarpophalangeal joint (MCP) of the index finger, the dorsum support 22 and proximal end which wraps around as the wrist support 24 are shown to be able to be fabricated from a single flat sheet of material.

Figure 5:
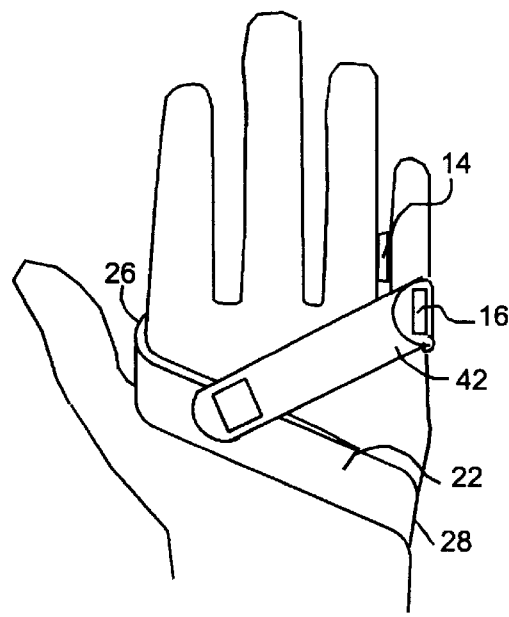
FIG. 5 is a front view of the back of the user's hand wearing a splint incorporating an additional support strap.
Figure 6:
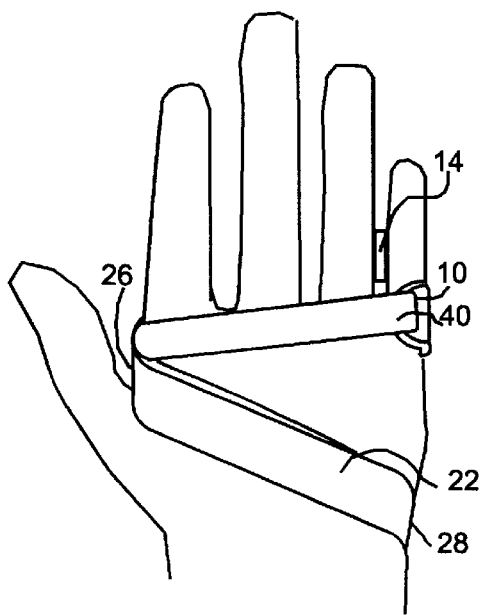
FIG. 6 is a front view of the back of the user's hand wearing the disclosed splint incorporating an alternate support strap.

Although the embodiment illustrated herein is manufactured from a single piece of material, multiple sections can be used which are connected through means which are convenient to the type of material used, i.e., hot melt glue, rivets, etc. Each of the splints should be molded to the specific user's hand to obtain maximum support and comfort. In some instances, additional straps 40 and 42 may be desired which can be added on either a permanent or temporary basis, as illustrated in FIGS. 5 and 6. The additional straps can be affixed to the splint 10 through use of hook and loop material. The illustrated straps are two examples of possible configurations and should, in no way, limit the scope of the invention. Although the support would not be as beneficial, the disclosed design can be manufactured from a combination of hook and loop material, fabric and semi-rigid inserts which are placed to provide the compression and extension required to achieve the three point support disclosed heretofore.

Various modifications of the invention regarding the placement of supports, contact areas, material types and widths may be necessary for individual patients by those skilled in the art of splinting or orthotics.

What is claimed is:

1. A splint to provide support to fingers on a user's hand said splint configured in a continuous spiral to apply pressure at three counterbalancing pressure points through contact at the finger's ulnar medial side, palm proximal the hand's metacarpophalangeal joints, dorsum of the hand, ulnar styloid and wrist, comprising:

at least one finger support member, each of said at least one finger support members positioned and configured to contact the finger's ulnar medial side, a palmar support member, said palmar support member shaped and configured to conform to the palm directly under the metacarpophalangeal joints, a radial arc member, said radial arc member shaped and configured to conform to the hand's radial area distal to the thumb and proximal to the metacarpophalangeal joint of an index finger, a dorsum support member, positioned to angle across the hand's dorsum, a proximal arc member, shaped and configured to conform to the hand's ulnar side distal the ulnar styloid, and a wrist support member, said wrist support member shaped and configured to conform to the user's forearm proximal the wrist and the thumb's carpometacarpal joint wherein said splint contacts the hand to apply pressure to the ulnar medial side of at least one finger of the user's hand, a web space between the thumb and the metacarpophalangeal joint of the index finger and to the wrist distal to the ulnar styloid, whereby pressure at said three counterbalancing pressure points provides ulnar support to the user's fingers.

2. The splint of claim 1 wherein said splint is one contiguous piece of semi-rigid material.

3. The splint of claim 2 wherein the palmar support is slightly arched to conform to said user's palmar arch.

4. The splint of claim 2 wherein said material is a plastic.

5. The splint of claim 2 wherein each of said at least one finger support member conforms to the contour of the ulnar medial side of the finger.

6. The splint of claim 2 wherein each of one of at least one finger support is in contact with the ulnar side of the user's little finger.

7. The splint of claim 2 wherein said material is metal.

8. The splint of claim 7 wherein said metal is covered with a resilient material.

9. The splint of claim 1 further comprising a hinged member attached to said wrist support to engage the forearm.

10. The splint of claim 1 wherein at least one of said at least one finger support member encircles the user's finger.

11. The splint of claim 1 wherein at least one of said at least one finger support member is padded.

12. The splint of claim 1 wherein said splint is at least two contiguous pieces, each of said at least two contiguous pieces being affixed to an adjacent contiguous piece.

13. The splint of claim 1 further comprising securing means, said securing means extending from one of said at least one finger support member to said dorsum support member.

14. The splint of claim 1 wherein said splint avoids contact with radial side of the hand's index finger metacarpophalangeal joint.

15. The splint of claim 1 wherein all surfaces of said splint are curved to match the hand's natural curve.

16. A spiral splint to provide lateral support to a user's fingers through contact with at least three points of the user's hand, said splint comprising a continuous spiral having a first end shaped to conform with at least one of the user's fingers, an approximate midpoint and a second end shaped to conform with the user's wrist, wherein said first end of said spiral is shaped and configured to contact the ulnar medial side of at least one finger at a first point, said approximate midpoint of said spiral is shaped and configured to contact the web space between the user's thumb and metacarpophalangeal joint of the user's index finger at a second point and said second end of said spiral is shaped and configured to contact the user's wrist distal the user's ulnar styloid at a third point, the configuration to contact the first, second and third points providing lateral support for the fingers through counterbalancing pressure points.

17. The splint of claim 16 wherein said pressure applied by said splint being shaped and configured to contact the ulnar medial sides of the fingers prevents ulnar medial deviation caused by the user's tendons slipping from the metacarpophalangeal joints.

18. The splint of claim 16 wherein said splint is shaped and configured to come in contact with the user's fingers during use thereby creating lateral force that is countered by contact by said splint at the web space which creates lateral force at said web space which is countered by said splint contacting said hand proximal said ulnar styloid, whereby said lateral force is distributed along said user's hand and wrist.

19. The splint of claim 16 wherein said splint is a contiguous spiral of semi-rigid material, said semi-rigid material being molded to conform to said user's hand.

20. The method of supporting a user's fingers in an position to allow for normal placement of tendons adjacent said user's metacarpophalangeal joints using a spiral splint for supporting fingers on a user's hand, said splint having at least one finger support in contact with said finger's ulnar medial sides; a palmar support engaging said user's palm directly under said hand's metacarpophalangeal joints; a radial arc conforming to and engaging the radial area of said user's said hand proximal said user's thumb and proximal to said metacarpophalangeal joint of said user's index finger; a dorsum support angling across said hand's dorsum; a proximal arc which engages said ulnar side of said hand proximal said ulnar styloid; a wrist support, which engages said user's forearm proximal said user's wrist and said thumb's carpometacarpal joint; comprising the steps of:

cutting a flat pattern of said spiral splint from a semi-rigid material;

arcing a first of said finger supports to conform to said user's little finger;

arcing subsequent finger supports to conform to said user's subsequent fingers;

arcing said splint to place said palmar support along said user's palm;

conforming said palmar support to said palm; forming a radial arc conforming to and engaging the radial area of said user's said hand proximal said user's thumb and proximal to said metacarpophalangeal joint of said user's index finger;

angling said splint from said metacarpophalangeal joint, across said hand's dorsum, to an area proximal said ulnar styloid;

arcing said splint at said area proximal said ulnar styloid;

curving said splint to engage said forearm proximal said thumb's carpometacarpal joint;

placing said first of said finger supports proximate said little finger's ulnar medial side;

placing said subsequent finger supports proximate the ulnar medial sides said subsequent fingers;

wrapping said wrist support around said forearm proximate said user's wrist and said thumb's carpometacarpal joint;

adjusting said splint to be in contact with ulnar medial side of one or more fingers, web space between said thumb and said radial side of the metacarpophalangeal joint of said user's index finger and said wrist proximal said ulnar styloid, whereby force exerted by said fingers on said finger supports is countered by said curve distal said web space, force from said web space is countered by said curve proximal said ulnar styloid, thereby providing lateral support for said fingers and repositions said tendons to a normal position adjacent said user's metacarpophalangeal joints and allowing for increased grip strength and a decrease in associated pain.

21. The method of applying support to fingers on a user's hand with a splint configured in a continuous spiral to apply pressure at three counterbalancing pressure points through contact at the hand's ulnar medial side, palm proximal the hand's metacarpophalangeal joints, dorsum of the hand, ulnar styloid and wrist, said splint comprising:

at least one finger support member, each of said at least one finger support members positioned and configured to contact the ulnar medial side of the user's finger, a palmar support member, said palmar support member shaped and configured to conform to the palm directly under the metacarpophalangeal joints of the user's finger, a radial arc member, said radial arc member shaped and configured to conform to the hand's radial area distal to the thumb and proximal to the metacarpophalangeal joint of an index finger of the user, a dorsum support member, positioned to angle across the dorsum of the user, a proximal arc member, shaped and configured to conform to the ulnar side of the user's wrist distal the ulnar styloid, and a wrist support member, said wrist support member shaped and configured to conform to the user's forearm proximal the wrist and the carpometacarpal joint of the user's thumb, comprising the steps of placing said at least one finger support member in contact with the ulnar medial side of the user's finger, placing said palmar support member in contact with the palm, placing said radial arc member between the user's thumb and index finger, placing said proximal arc member in contact with the ulnar side of the user's wrist, placing said wrist support member around the user's forearm, wherein said splint in use comes in contact with the user's hand to apply pressure to the ulnar medial side of at least one finger, a web space between the thumb and the metacarpophalangeal joint of the index finger and to the wrist distal to the ulnar styloid, whereby pressure at said three counterbalancing pressure points provides ulnar support to the fingers.

22. The method of providing lateral support to a user's fingers through contact of a spiral splint with at least three points of the user's hand, the at least three points including:

the ulnar medial side of at least one finger, the web space between the user's thumb and the user's metacarpophalangeal joint of the user's index finger, and the user's wrist distal the user's ulnar styloid, wherein a first end of said spiral contacts the ulnar medial side of at least one finger, an approximate midpoint of said spiral contacts the web space and a second end of said spiral contacts the wrist, the contact at these three points providing lateral support for the fingers through counterbalancing pressure points.

* * * * *